US010912915B2

(12) United States Patent
Argaman (10) Patent No.: US 10,912,915 B2
(45) Date of Patent: Feb. 9, 2021

(54) APPARATUS, SYSTEM AND METHOD OF MULTISENSORY STIMULATION

(71) Applicant: Itai Argaman, San Francisco, CA (US)

(72) Inventor: Itai Argaman, San Francisco, CA (US)

( * ) Notice: Subject to any disclaimer, the term of this patent is extended or adjusted under 35 U.S.C. 154(b) by 137 days.

(21) Appl. No.: 14/931,241

(22) Filed: Nov. 3, 2015

(65) Prior Publication Data

US 2017/0119994 A1    May 4, 2017

(51) Int. Cl.
*A61M 21/00* (2006.01)
*A61B 5/0205* (2006.01)
*A61B 5/0476* (2006.01)
*A61B 5/08* (2006.01)
*A61B 5/024* (2006.01)
*A61B 5/00* (2006.01)
*A61B 8/00* (2006.01)

(52) U.S. Cl.
CPC .......... *A61M 21/00* (2013.01); *A61B 5/0205* (2013.01); *A61B 5/024* (2013.01); *A61B 5/0476* (2013.01); *A61B 5/08* (2013.01); *A61B 5/4836* (2013.01); *A61B 5/4848* (2013.01); *A61B 5/7475* (2013.01); *A61B 8/4281* (2013.01); *A61M 2021/005* (2013.01); *A61M 2021/0022* (2013.01); *A61M 2021/0027* (2013.01); *A61M 2021/0066* (2013.01); *A61M 2205/3653* (2013.01); *A61M 2205/502* (2013.01); *A61M 2230/06* (2013.01); *A61M 2230/10* (2013.01); *A61M 2230/42* (2013.01)

(58) Field of Classification Search
None
See application file for complete search history.

(56) References Cited

U.S. PATENT DOCUMENTS

| 5,101,810 | A | | 4/1992 | Skille et al. |
| 5,266,070 | A | | 11/1993 | Hagiwara et al. |
| 5,373,565 | A | * | 12/1994 | Watanabe ............... H04R 1/24 381/182 |
| 5,441,476 | A | * | 8/1995 | Kitado .................. A61M 21/00 600/21 |
| 5,725,472 | A | | 3/1998 | Weathers |

(Continued)

FOREIGN PATENT DOCUMENTS

| DE | 20 2009 002 043 U1 | 7/2009 |
| EP | 2 666 505 A1 | 11/2013 |

(Continued)

*Primary Examiner* — Christine H Matthews
(74) *Attorney, Agent, or Firm* — Browdy and Neimark, P.L.L.C.

(57) ABSTRACT

In an exemplary embodiment, a body-supporting structure for multisensory stimulation may be provided. The body-supporting structure for multisensory stimulation may include a number of biometric measurement devices for detecting a user's state and a number of speakers or transducers connected to resonators on the body-supporting structure and arranged to transfer a stimulus in accordance with the state detected. A computing device may be connected to the biometric measurement devices and to a virtual reality display. A number of input devices may also be connected to the computing device and to a number of amplifiers configured to transfer a signal to the number of speakers and transducers.

17 Claims, 7 Drawing Sheets

(56) References Cited

U.S. PATENT DOCUMENTS

| | | | | |
|---|---|---|---|---|
| 6,012,926 A | * | 1/2000 | Hodges | A61M 21/00 |
| | | | | 434/236 |
| 6,702,767 B1 | | 3/2004 | Douglas et al. | |
| 8,932,218 B1 | | 1/2015 | Thompson | |
| 2011/0055720 A1 | | 3/2011 | Potter et al. | |
| 2011/0245586 A1 | | 10/2011 | Slane | |
| 2011/0251535 A1 | * | 10/2011 | Bender | A61M 21/02 |
| | | | | 601/49 |
| 2013/0261378 A1 | | 10/2013 | Habiche | |
| 2014/0206929 A1 | | 7/2014 | Anderson et al. | |
| 2017/0080246 A1 | * | 3/2017 | Knight | A61N 5/06 |

FOREIGN PATENT DOCUMENTS

| | | |
|---|---|---|
| WO | 2006003269 A1 | 1/2006 |
| WO | 2012011869 A1 | 1/2012 |
| WO | 2014006596 A1 | 1/2014 |
| WO | 2015006163 A1 | 1/2015 |
| WO | 2015028480 A1 | 3/2015 |

* cited by examiner

| SSG-Fader | state | frequency | background | sounds |
|---|---|---|---|---|
| | Gamma ⇧ | | ⇧ | Instruments and complex sounds ⇧ |
| | Alpha-Theta ⇧ | | thunder and heavy rain ⇧ | Chords and multiple OSC ⇧ |
| | Theta ⇧ | 4 Hz - 6 Hz ⇧ | light rain ⇧ | 3D tones ⇧ |
| | Theta-Delta ⇧ | 2 Hz - 4 Hz ⇧ | peaceful forest day ⇧ | tibetan bowl ⇧ |
| | Delta ⇧ | 0.1 Hz - 2 Hz ⇧ | white noise ⇧ | pure tone ⇧ |
| | quiet | quiet | quiet | quiet |

APPARATUS, SYSTEM AND METHOD OF MULTISENSORY STIMULATION

BACKGROUND

Vibroacoustic therapy may combine sounds and music selected to resonate in specific areas of the body. Layers of binaural beats may be added to music and low frequency pulses to promote deep relaxation. The sound vibrations may be administered through specially designed speakers or transducers built into a piece of furniture or a body-supporting structure such as a recliner, beanbag, mattress, pad, or a table. There may be several benefits to health and well-being from the experience of feeling the sounds and vibrations provided by the vibroacoustic treatment. Vibroacoustic therapy alone, or associated with binaural beats may be helpful for a variety of severe conditions such as sports injury, muscular strain or post-surgery, as well as chronic conditions such as asthma, arthritis, menstrual pain and stress.

SUMMARY

In an exemplary embodiment, a body-supporting structure for multisensory stimulation may be provided. The body-supporting structure for multisensory stimulation may include a number of biometric measurement devices for detecting a user's state and a number of speakers or transducer connected to resonators on the body-supporting structure and arranged to transfer a stimulus in accordance with the state detected. A computing device may be connected to the biometric measurement device and to a virtual reality display. A number of input devices may also be connected to the computing device and to a number of amplifiers configured to transfer a signal to the number of speakers and transducers In a second exemplary embodiment, a method of providing multisensory stimulation may be provided. The method of providing multisensory stimulation may include providing a body-supporting structure for multisensory stimulation, placing a user in physical contact with the body-supporting structure and operating the at least one input device and the amplifier so as to expose the user to vibration and sounds from at least one of the at least one speakers and at least one the transducer. The body-supporting structure for multisensory stimulation may include a number of biometric measurement devices for detecting a user's state and a number of speakers or transducer connected to resonators on the body-supporting structure and arranged to transfer a stimulus in accordance with the state detected. A computing device may be connected to the biometric measurement device and to a virtual reality display. A number of input devices may also be connected to the computing device and to a number of amplifiers configured to transfer a signal to the number of speakers and transducers

BRIEF DESCRIPTION OF THE DRAWINGS

Advantages of embodiments of the present invention will be apparent from the following detailed description of the exemplary embodiments. The following detailed description should be considered in conjunction with the accompanying figures in which.

DETAILED DESCRIPTION

Aspects of the present invention are disclosed in the following description and related figures directed to specific embodiments of the invention. Those skilled in the art will recognize that alternate embodiments may be devised without departing from the spirit or the scope of the claims. Additionally, well-known elements of exemplary embodiments of the invention will not be described in detail or will be omitted so as not to obscure the relevant details of the invention.

As used herein, the word "exemplary" means "serving as an example, instance or illustration." The embodiments described herein are not limiting, but rather are exemplary only. It should be understood that the described embodiments are not necessarily to be construed as preferred or advantageous over other embodiments. Moreover, the terms "embodiments of the invention", "embodiments" or "invention" do not require that all embodiments of the invention include the discussed feature, advantage or mode of operation.

Further, many of the embodiments described herein may be described in terms of sequences of actions to be performed by, for example, elements of a computing device. It should be recognized by those skilled in the art that the various sequence of actions described herein can be performed by specific circuits (e.g., application specific integrated circuits (ASICs)) and/or by program instructions executed by at least one processor. Additionally, the sequence of actions described herein can be embodied entirely within any form of computer-readable storage medium such that execution of the sequence of actions enables the processor to perform the functionality described herein. Thus, the various aspects of the present invention may be embodied in a number of different forms, all of which have been contemplated to be within the scope of the claimed subject matter. In addition, for each of the embodiments described herein, the corresponding form of any such embodiments may be described herein as, for example, "a computer configured to" perform the described action.

Figure 1:
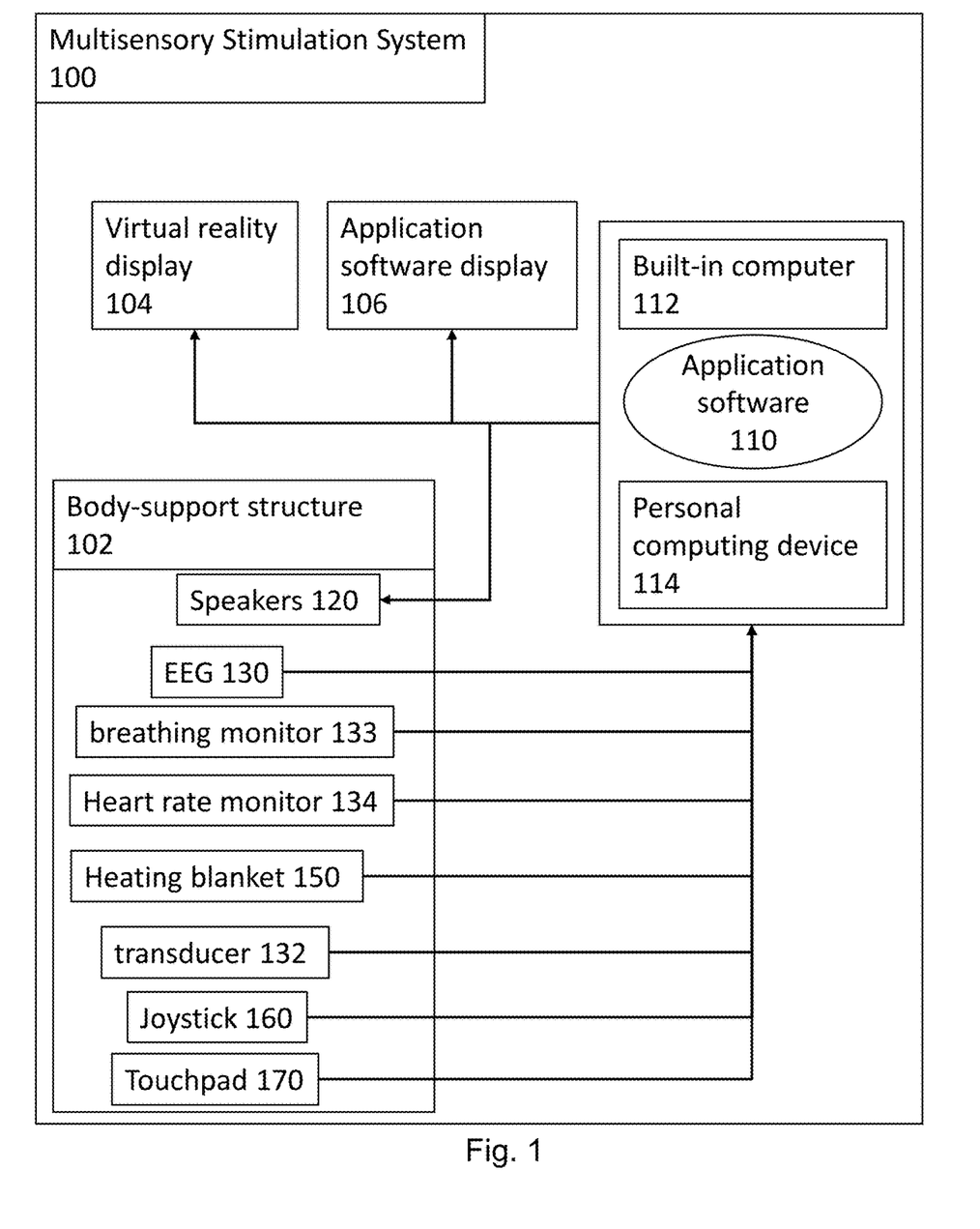
FIG. 1 is a diagram showing an exemplary embodiment of a multisensory stimulation system.

In an exemplary embodiment illustrated in FIG. 1, the multisensory stimulation system 100 may include a computing device such as a built-in computer 112 or a personal computing device 114 that may run an application software 110. The personal computing device 114 may include, but not be limited to, a laptop, a smartphone, a desktop, and a tablet that may be connected to the multisensory stimulation system 100. An application software 110 may be used to control the multisensory stimulation system 100 functionalities. The personal computing device 114 may be connected to the multisensory stimulation system 100 using a mobile dock, a USB cable, or by remote connectivity such as, BLUETOOTH or wireless internet, as would be understood by a person having ordinary skill in the art. Once the user's phone may be connected it may not function as a phone, it may not be able to receive calls or messages so the user is not interrupted during the session. The user may have to give permission to disable communication features before the application software 110 may be launched. Further, the multisensory stimulation system 100 and the application software 110 may be configured to receive updates using an internet connection. The application software 110 may be available separately and may be downloadable from a website or an application software store. The application software 110 may be used on its own and may allow the user to have a session while away from the multisensory stimulation system.

Still referring to FIG. 1, the multisensory stimulation system 100 may include a body-supporting structure 102 providing a relaxing posture such as, but not limited to, a chair, a recliner, or a bed. The multisensory stimulation system 100 may be connected to a number of other devices such as, but not limited to electroencephalography systems (EEG) 130, a breathing monitor 133, a heart rate monitor 134, a heating blanket 150, transducers 132, a touchpad 170, joystick 160 or the like. Further, a virtual reality display 104 and an application software display 106 may be connected to the built-in computer 112 or to the personal computing device 114.

Figure 2A:
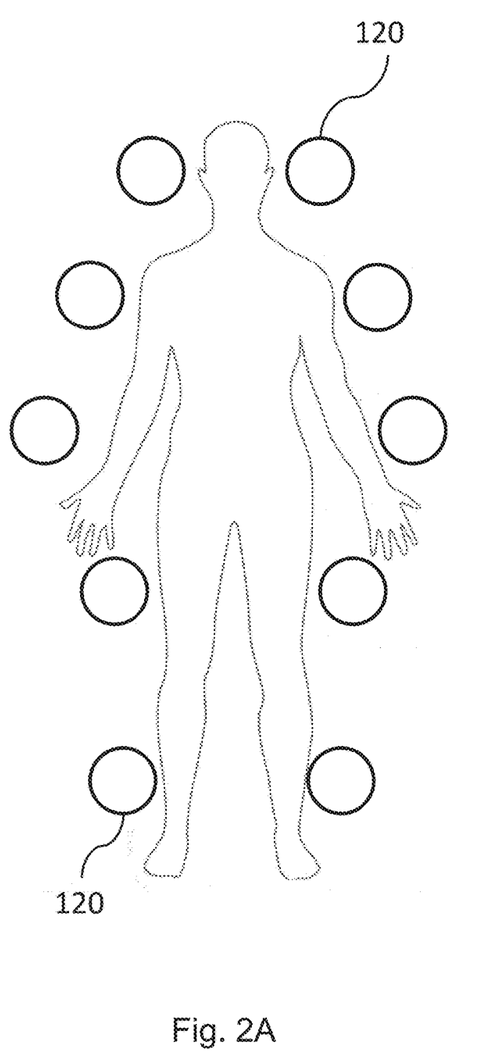
FIG. 2A is a diagram showing an exemplary embodiment of a 10 speakers configuration.
Figure 2B:
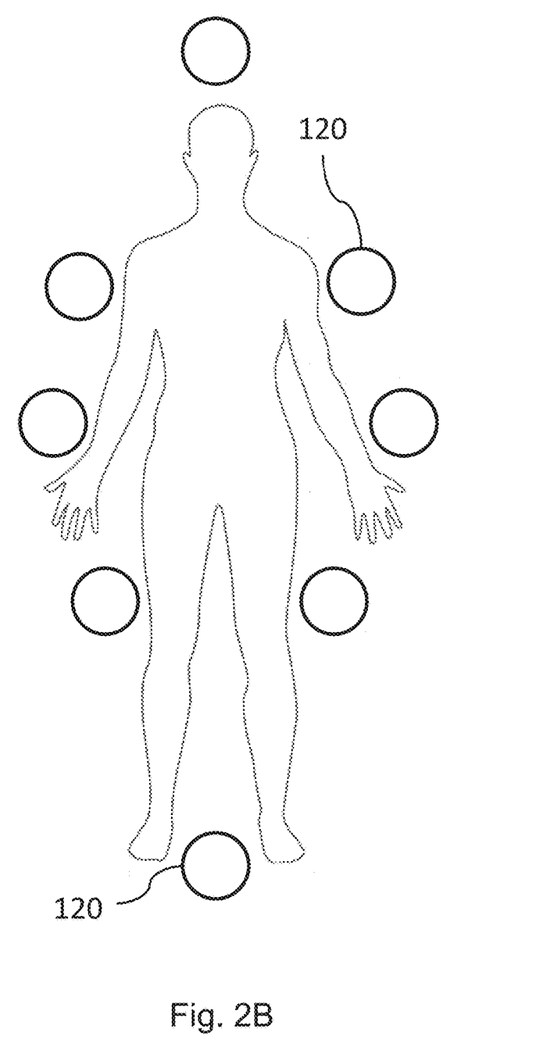
FIG. 2B is a diagram showing an exemplary embodiment of an 8 speakers configuration.

In an exemplary embodiment illustrated in FIGS. 2A and 2B, the multisensory stimulation system 100 may include a number of speakers 120. The speakers 120 may be disposed evenly along the body in a 10-speakers configuration (FIG. 2A) or in an 8-speakers configuration (FIG. 2B) or any number of pairs. The speakers 120 may be associated in pairs for stereo signal rendering. It may be appreciated that any desired configuration and number of speakers may be connected to the multisensory stimulation system 100, as may be understood by a person having ordinary skill in the art.

Figure 3:
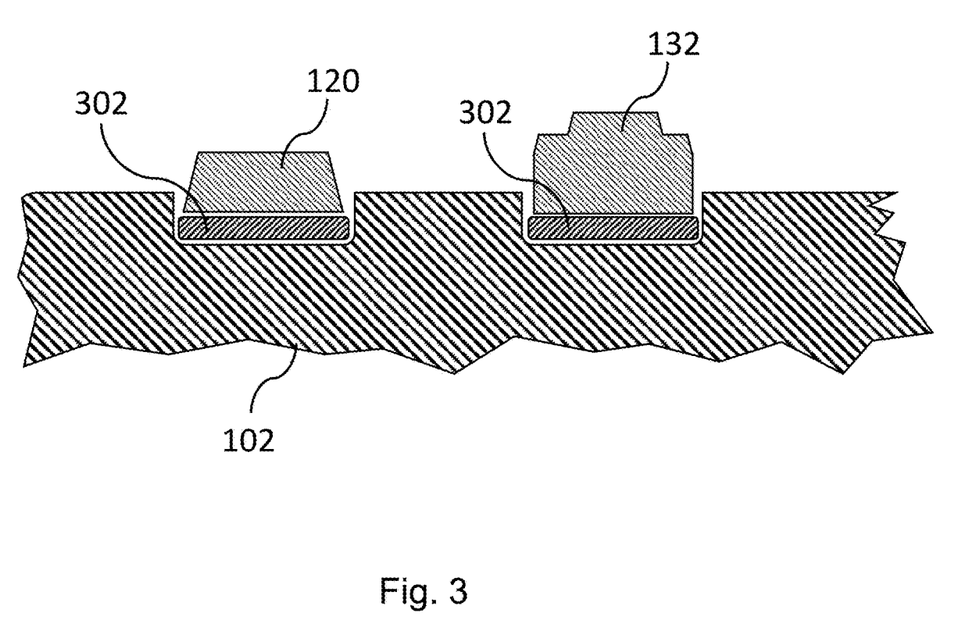
FIG. 3 is a diagram showing an exemplary embodiment of speaker and transducer connected to a body supporting element.

In an exemplary embodiment illustrated in FIG. 3, each speaker 120 or transducer 132 may be rigidly connected to a resonator 302. It may be appreciated that the resonator surface may be of any desired materials including, but not limited to, wood, metal, and polymer, as may be understood by a person having ordinary skill in the art. Additionally, each speaker 120 or transducer 132 may be isolated from each other so as to contain the sound within a desired location and prevent vibrations from being spread around the body-supporting structure 102.

The multisensory stimulation system 100 may create multiple audio channels and feed each channel to a specific speaker or to headphones. The multisensory stimulation system 100 may also include dedicated hardware, cables, and devices that may divide signals and create multiple outputs for the headphones and speakers. Different sounds may be sent to individual speakers 120 so as to target specific locations in the body. For example, a sound may be sent to a number of speakers 120 located near the chest and may be panned slightly to the left to focus most of the sound energy to the heart. In a further example, the multisensory stimulation system 100 may circulate the vibrational frequencies by connecting one oscillator to the left speaker and a second oscillator to the right speaker.

Figure 4:
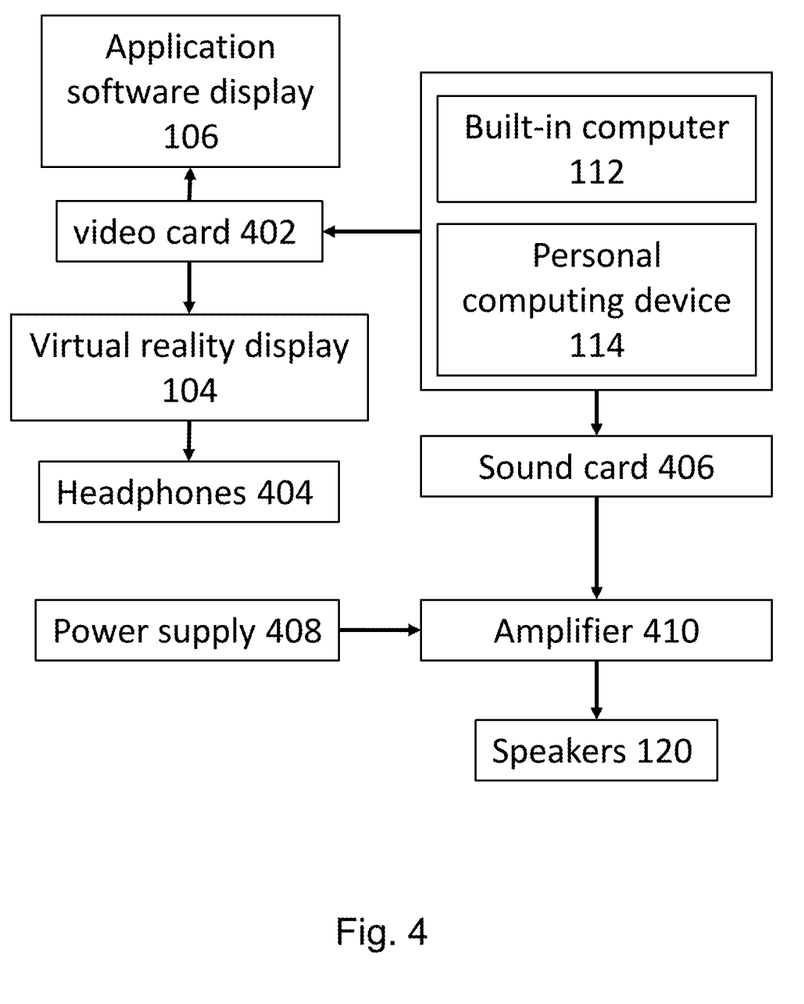
FIG. 4 is a diagram showing an exemplary embodiment of electronic elements connections.

In an exemplary embodiment illustrated in FIG. 4, the built-in computer 112 or the personal computing device 114 may be connected to a graphic or video card 402 that may send data to the application software display 106 and to the virtual reality display 104. Headphones may optionally be connected to the virtual reality display 104 or directly to the sounds device and synchronize to the visuals from the virtual reality display. The built-in computer 112 or the personal computing device 114 may further be connected to a sound card 406 that may send signals to an amplifier 410 connected to a power supply 408. The amplifier board 410 may then feed the amplified sound to a number of speakers 120.

The multisensory stimulation system 100 may create complex routing to the speakers 120 and may bring vibrational circulation around the body so as to release stuck energy and emotion. The vibrational circulation may help the blood circulating and massage the nervous system. Because of its vibrational nature, the sound may penetrate deeply into the body and may release deep tensions impervious to regular massages.

Binaural recording (or other 360 surround sound recording method) is a method of recording sound that may use two microphones, arranged with the intent to create a 3D stereo sound, or surround sound effect. It may be appreciated that more than two microphones may be utilized such as b-format method using a four-channel microphone, 32 microphones systems, or any desired technology designed to obtain better and accurate 360-surround recording. The surround sound may give to the user the impression of being immersed in the sound. For example, the user may have the impression of actually being in a room with performers playing music. This effect may be created using a technique known as "dummy head recording", wherein a mannequin head is outfitted with a microphone in each ear. Binaural recording may be primarily intended for replay using headphones.

In an exemplary embodiment, the application software 110 may create binaural sounds even if the sounds were not recorded with dummy head or 3D microphones. The application software 110 may use binaural technology so as to reproduce psychoacoustic sound or virtually created 360 spaces and environment. The application software 110 may use specialized tools such as, but not limited to, digital signal processing (DSP) technology for creating realistic 3D soundscapes using regular stereo sound. The application software may combine HRTF-based audio panning with acoustic environment modeling, and may include, but not be limited to wall reflections, reverberation, distance modeling, and the Doppler pitch effect. The HRTF may be a linear function is based on the sound source's position and may take into account many of the cues humans use to localize sounds. The HRTF may be used to develop pairs of finite impulse response (FIR) filters for specific sound positions; each sound position may require two filters, one for the left ear, and one for the right. Thus, to place a sound at a certain position in virtual space, the set of FIR filters that correspond to the position may be applied to the incoming sound, yielding spatial sound. The computations involved in convolving the sound signal from a particular point in space may require specialized equipment. The 3D soundscape may be synchronized to the visuals on the virtual reality display 104. The application software 110 may create a virtual 3D space from a stereo signal. However, it may be appreciated that the application software 110 may use any desired technological solution for creating and reproducing a 3D, or 360° sound image from a single sound source, as may be understood by a person having ordinary skill in the art.

Further, the application software 110 may virtually direct the sounds to a specific position in space or in the user's brain and body.

In an exemplary embodiment, unique surround sounds may be recorded with 360° or binaural recording equipment in different places or spaces such as during a walk in nature, playing crystal bowls or the like. Multiple tones may play together to create sound octaves and therapeutic harmonies by the sacred geometry intervals. The multisensory stimulation system 100 may also control low pass filters so as to achieve a smooth fade in and out between sounds, and may be combined with controls of the volume fade in and out.

In another exemplary embodiment, the multisensory stimulation system 100 may include a virtual reality display 104. The display may include 3D capabilities, such as a 3D screen and 3D headgear, augmented reality, and holograms as may be understood by a person having ordinary skill in the art. The virtual reality display 104 may show virtual places, spaces, shapes, colors, or the like. Images shown in the virtual reality display 104 may correspond to frequencies generated by the multisensory stimulation system 100.

In a further exemplary embodiment, the image shown on the display may be related to, and synchronized with, the session. For example, the sound of a walk in the forest may be associated with forest visuals shown on the display or a shape may flicker on and off by the same frequency rate as the binaural beats that may be playing. A physical or digital tapping device or the touchpad 170 may allow the user to tap a desired tempo that may be used to adjust session parameters. Sessions may be rated by the user and the multisensory stimulation system 100 may configure new sessions according to ratings and may send feedback to a third party for future adjustments and monitoring The multisensory stimulation system 100 may provide therapeutic treatment during dedicated periods of time defined as sessions. Each session may be paused or canceled. If a user cancels the session, the sound may fade out until quiet. During the session, the volume of the sound may be controlled by a digital or analog volume knob, touchpad 170, joystick 160, or the like. The session may fade out and the multisensory stimulation system 100 may shut itself off when the user is not on the body-supporting structure 102, as may be detected by motion or weight sensors that may be connected to the multisensory stimulation system 100. In an exemplary embodiment, a human voice or a video shown on the virtual reality display 104 (for example, 3D headgear) may guide and direct the user before during and after the session.

Figure 5:
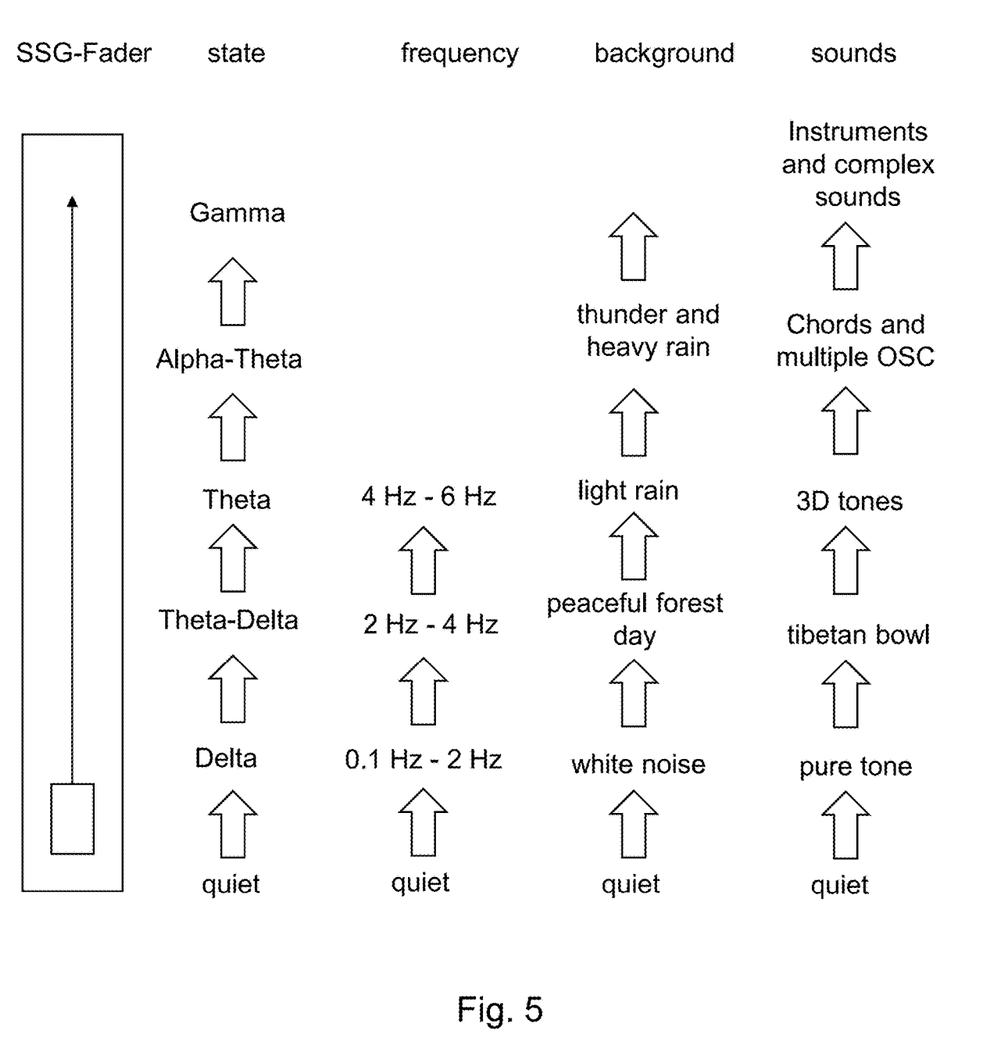
FIG. 5 is a diagram showing an exemplary embodiment of sounds and frequencies produced by the fader and their associated states.

In an exemplary embodiment, illustrated in FIG. 5, the application software 110 may provide a physical or digital fader allowing the user to modify the session in real time. The fader may provide the user with the ability to modify his current state or to change the session properties in a unique and simple way. Further, the session properties may be modified while laying, sitting, and even with closed eyes, as may be understood by a person having ordinary skill in the art. The fader settings may be changed, for example, by simple interaction with a touchpad 170. The fader and may be designed and configured to minimize movements and mental efforts required to change the settings. The fader may be referred to as a self state generator (SSG) used to modify the user's state by increasing or decreasing the fader values. It may be appreciated that what is referred to as the "user's state" or "state" may include, but not be limited to, mental state, state of mind, state of consciousness, mood, focus, and disposition, as may be understood by a person having ordinary skill in the art. Modification of the fader's parameters may modify frequencies and tone pitches so as to achieve complex sounds, as may be understood by a person of ordinary skill in the art. The multisensory stimulation system 100 may allow the user to tune instinctively the sound properties to attain a desired state. Higher frequencies may be responsible for creativity, focus, higher memory skills, and awareness. Whereas the lower frequencies may be responsible for the sleep state, relaxing state, healing state, meditative state, underworld state, internal state, and spiritual state.

In an exemplary embodiment, a circulation effect may be achieved when using frequencies of approximately 30 Hz on a left speaker and approximately 31 Hz on a right speaker. This circulation effect may be caused by the binaural effect, as the right frequencies may be increased, a feeling of faster circulation may be achieved. The multisensory stimulation system 100 may have a number of oscillators that may produce specific frequencies and may play concurrently with other oscillators. When the frequency difference between the oscillators is between approximately 0.1 Hz to approximately 30 Hz, binaural beats may be created. The lowest frequency produced by the fader may be approximately 0.1 Hz. The frequency of approximately 0.1 Hz may be created by having a first oscillator set to approximately 100 Hz and a second oscillator set to approximately 100.1 Hz. Similarly, a cycle of 8 Hz (alpha range) may be obtained if the second oscillator increases the frequency from approximately 100.1 Hz to approximately 108 Hz. The fader may be virtually divided into an infinite number of steps that may have different session parameters. The vibrations generated by the multisensory stimulation system 100 may be of low frequencies to high frequencies of approximately 20,000 Hz. Further, each frequency may be modified within each fader step and modifications of the fader steps may modify frequency cycles and background sounds. Background sounds of a storm or heavy ocean may be associated with a frequency in the beta or gamma range of approximately 30 Hz that may correspond to a state of awakening.

In a further exemplary embodiment, the multisensory stimulation system 100 may use unique and specific tones such as, but not limited to, binaural beats, pure sin waves, random sounds, atmosphere sounds, weather sounds, 3D sounds, and vibrations that may be mixed together and may be directed to specific internal and external body parts. The sound sources may not be limited to the technology currently available and may be created using other external sources that produces sound. The sound frequencies may be delivered to the user from any direction, and may not be limited to front, back, above, and below the user, as would be understood by a person having ordinary skill in the art.

A number of other functions and benefits may be associated with the body-supporting structure 102. In an exemplary embodiment, the multisensory stimulation system 100 may include a number of ultrasonic transducers and a number of transducers 132 so as to use frequencies greater than the upper limit of human hearing (approximately greater than 20 kHz). It may be appreciated that a number of conditions may be treated with ultrasounds, including, but not limited to ligament sprains, muscle strains, tendonitis, joint inflammation, plantar fasciitis, metatarsalgia, facet irritation, impingement syndrome, bursitis, rheumatoid arthritis, osteoarthritis, and scar tissue adhesion. Further, ultrasounds may be used in a number of biomedical applications such as breaking up stony deposits or tissue, and accelerating the effect of drugs in a targeted area as may be understood by a person having ordinary skill in the art. Further, the multisensory stimulation system 100 may include, but not be limited to element typically found in medical ultrasound devices such as a transducer, a transmitter pulse generator, compensating amplifiers, control units for focusing, digital processors and display monitor as would be understood by a person having ordinary skill in the art.

Ultrasound waves may be applied to tissues using a round-headed wand or transducer that is in direct contact with the user's skin. Gel may be used on all surfaces of the transducer's head to reduce friction and assist transmission of the ultrasonic waves. The waves may be generated by piezoelectric effect caused by the vibration of crystals within the head of the wand or probe. The ultrasonic waves that pass through the skin may cause a vibration of the local tissues. This vibration or cavitation may cause a deep heating locally though typically no perception of heat may be felt by the patient.

Therapeutic ultrasound in physical therapy may involve alternating compression and rarefaction of sound waves with a frequency of >20 KHz. Therapeutic ultrasound frequency used may be from approximately 0.7 MHz to approximately 3.3 MHz. The maximum energy absorption in soft tissue may occurs from approximately 2 cm to approximately 5 cm. The intensity may decrease as the waves penetrate deeper and are absorbed by connective tissue: ligaments, tendons, and fascia (and also by scar tissue).

Figure 6:
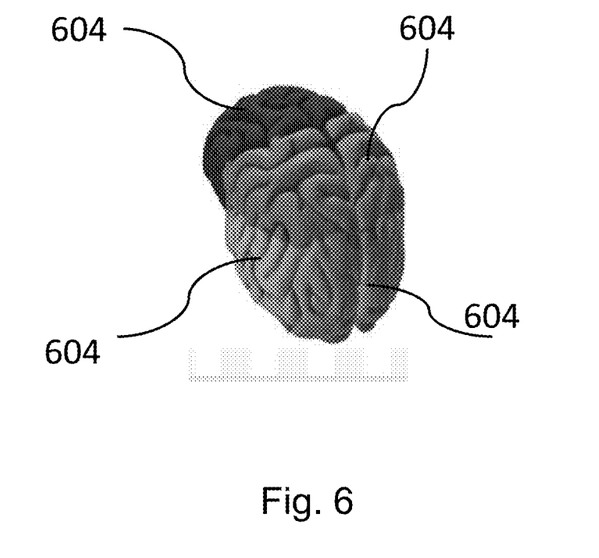
FIG. 6 is a diagram showing an exemplary embodiment of a brain representation.

In an exemplary embodiment, illustrated in FIG. 6, the multisensory stimulation system 100 may use a 360 panner (for example, HRTF technologies) to send frequencies to different parts of the head and brain so as to virtually stimulate the targeted area. A 3D image (shown in FIG. 6) may be displayed on the application software display 106 or the virtual reality display 104 and the user may interact with the application software 110 and the image by using the joystick 160 or brainwaves. The 3D image may display information about the various parts of the brain. For example, stimulation of one of the four lobes 604 of the brain may help the user to focus. The stimulation parameters may be controlled in real time or may be set before the session begins. A unique surround panner may move the sounds toward the speakers 120 or the headphones may be part of the multisensory stimulation system 100 in order to move the sounds around the body so as to focus the sound on a specific body area. A pre-programmed session may circulate and steer the sound in a specific pattern over the body.

In another exemplary embodiment, a session focusing on treating the spine may deliver sounds and vibration directly to the spine. The sounds and vibrations may also move around the spine so as to release tension and to stimulate a specific area. Other pre-programmed sessions may focus on other areas of the body including, but not limited to the digestive system, lungs, heart, and scalp. The sound may travel over the meridians, energy points and other critical and potential points that may bring deep healing to those areas, as may be understood by a person of ordinary skill in the art.

Figure 7A:
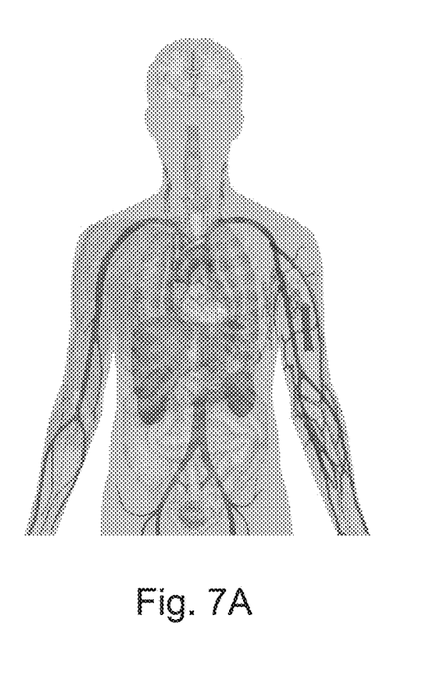
FIG. 7A is a diagram showing an exemplary embodiment of a body and organ representation.
Figure 7B:
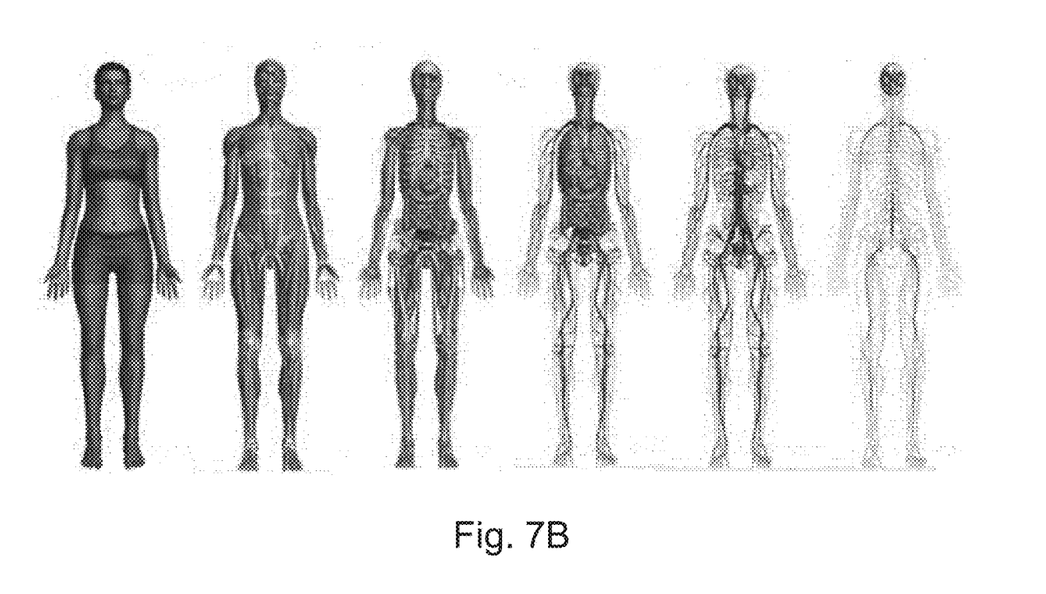
FIG. 7B is a diagram showing an exemplary embodiment of a body and organ representation.

In another exemplary embodiment illustrated in FIGS. 7A and 7B, the application software 110 may show views of the human body in the application software display 106 or in the virtual reality display 104. The user may turn around, spin, and zoom in and out of the virtual body. Various structural and functional features of the body may be displayed with their corresponding names, for example: name of the main muscles, internal organs, bones, or chakras. Further, the user may get an explanation of how the body may be functioning by clicking on a specific body area. Further sounds may be directed to any desired location by selecting the target area on the image displayed.

In another exemplary embodiment, the multisensory stimulation system 100 may be designed as a portable device for personal use. The portable device may be controlled using a portable computing device such as, but not limited to, a smartphone or a tablet and may operate without additional audio device or soundwave generator. A main audio signal originating from the portable computing device may be duplicated into two identical audio signals, a first audio signal, and a second audio signal. The duplication, or splitting, of the main audio signal may be achieved, for example, by using a device similar to the devices commonly used to split an audio output for the simultaneous use of two sets of headphones. The first audio signal may pass through an analog or digital low pass filter so as to filter high frequencies and send only the low frequencies to a number of speakers 120. The second audio signal may pass through an analog or digital high pass filter so as to send only high frequencies to headphones. It may be appreciated that any desired filters may be applied to the first audio signal and second audio signal as might be understood by a person having ordinary skill in the art. Further, the portable device designed for personal use may retain all the functions and benefits of the multisensory stimulation system 100.

In another exemplary embodiment, ultrasound technology may be applied to show the user's actual internal body in real time, this functionality may allow physicians and healthcare specialists to visualize how the sounds and vibrations may affect the area. Medical imaging renditions and scans may be displayed in real time on the virtual reality display 104 or application software display 106, as would be understood by a person having ordinary skill in the art. It may be appreciated that any desired technique such as, but not limited to, image integration and image augmentation may be implemented.

In a further exemplary embodiment, the user may visualize, select, and modify the session parameters using a joystick 160, an EEG 130 feedback device, or any other desired technology that may allow reading the user's biometric signals or brainwaves and translating them into movement or to action in the environment. It may be appreciated that any systems capable of utilizing software or devices with brainwaves may be connected to the multisensory stimulation system 100, as may be understood by a person of ordinary skill in the art.

In an exemplary embodiment, a human body illustration may be displayed on the screen allowing the user to select a specific area to be treated. An external or digital joystick 160 may be used to navigate the application software 110, and move in the virtual reality display 104 in real time during the session and direct stimulation to specific body area or to internal energy spots.

Any desired sensors may be connected to the multisensory stimulation system 100 and may send information back to the software application. Such sensors may include, but not be limited to, breathing monitor 133, heart rate monitor 134, or the like. Feedback from these sensors may affect the sound in real time or may just be documented for monitoring purposes.

In an exemplary embodiment, feedback from a breathing monitor 133 may be used to modify the session in real time according to the user breathing cycles. For example, when the breathing cycles are slow, the session may produce a quiet sound with low frequencies and low vibrations. This session setting may maintain the user's current state according to a predetermined session program. Further, random sounds may be selected according to feedback from the breathing monitors 133 and may fade in and out during the session. The multisensory stimulation system 100 may produce different tones and sounds to maintain or change a present state.

In an exemplary embodiment, the user may select a desired mood from the application software display 106 or through the virtual reality display 104 and the application may create a unique session to bring the user to the chosen mood. The application may also modify or create sounds and sessions according to a shape that the users may draw on the touchpad 170.

In an exemplary embodiment, each session may be built like an original story or a journey with a start, a middle, and an end. The session may be divided into a number of time periods, for example, period 0 (zero) to period 10. Each period may have a specific duration and may be associated to a variety of sounds that may fade in. Periods may overlap and may be combined together depending on their functionalities. For example, period 1 may be at the beginning of the session, and may produce the first sound layers or vibrations. The session may be divided into percentages of the total duration, a full session may be 100%, and each period may correspond to predetermined percentages of the session. For example, the period 1 may correspond to the first 5% of the session and period two may be from approximately 5% to approximately 10%. Further, the duration of the session may be modified by the user at any time. When the user selects a different session duration, the new session duration may be set as 100% of the session and each period duration may be adjusted according to their relative percentages.

The application software 110 may propose games or tasks in the virtual reality display 104 that the user need to solve in order to improve a number of brain functionalities such as, but not limited to focus, memory, sharpness, and relaxation as may be understood by a person having ordinary skills in the art. During the session, the application software 110 may provide the user an option for active involvement in the narrative the story or for example to virtually walk to an area and move things or solve problems using brainwaves. The session may be designed to heal, relax, sleep, rehabilitate, play, educate, and improve brain skills in general. The session may also provide tasks to improve post trauma issues such as fear. For example, in treating fear of height, the multisensory stimulation system 100 may bring the user to a cliff of a mountain in order to face his or her fear and be able to confront it for healing purposes. Similar fear such as aircraft flight, hospitals, water, and animals may be treated in a similar way.

In an exemplary embodiment, the main background sound may be changed by the actuation of a digital or analog button. For example, a forest sound may randomly be changed to an ocean sound. The multisensory stimulation system 100 may generate a random session every time and may be adapted for children or according the user's needs. Further, the multisensory stimulation system 100 may separate vibrations and sounds that goes to the user headphones or to the speakers 120 into individual channels which may be controlled separately and bring more complexity and depth to the session. Further, the visuals shown on the virtual reality display 104 or on a software application display 106 may be synchronized with the sounds.

In at least one exemplary embodiment, the multisensory stimulation system 100 may release fragrances that may be associated with the visuals, for example if the user sees ocean visuals on the virtual reality display 104 or on the application software display 106, the multisensory stimulation system 100 may produce ocean fragrances. It may be appreciated that any desired fragrance may be produced, such as, but not limited to, ocean, forest, mountain, city, farm, temple, flowers, and food, as may be understood by a person having ordinary skill in the art. The multisensory stimulation system 100 may include elements of digital scent technology, such as, but not limited to, olfactometers, electronic noses, scent generating devices, synthetic and natural odor cartridges, and aroma mixers, as may be understood by a person having ordinary skill in the art.

In another exemplary embodiment, unique sounds recordings during a walk in nature or in different places may bring movement and changing surrounding so as to keep the user focused when a state of awareness is required. Perceived movement may help disabled people with walking disabilities by activating the lobe in their brain controlling movement. The design of the multisensory stimulation system 100 may allow the user lay down, sit, stand, or move during the session.

In another exemplary embodiment, the multisensory stimulation system 100 may be adapted to a variety of structures such as, but not limited to, airplane body-supporting structures, gaming devices, vehicle seats, medical equipment, baby seat, baby beds, baby toys, office chairs, and personal beds. A connection kit may be utilized to adapt the multisensory stimulation system 100 to the user's furniture. The connection kit may include speakers 120, and all the necessary hardware to connect the system to a built-in computer 112 or the user's personal computing device 114. The multisensory stimulation system 100 may be portable, customizable, and may be adapted to be used and integrated with other systems, as may be understood by a person having ordinary skill in the art. In an exemplary situation, an aviation company may integrate part of the multisensory stimulation system 100 functionality and technology to their own vibroacoustic airplane seats or beds.

The foregoing description and accompanying figures illustrate the principles, preferred embodiments, and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims.

What is claimed is:

1. A system for multisensory stimulation comprising:
   at least one biometric measurement device for detecting a user's state;
   headphones for providing an auditory output to the user;
   a body-supporting structure for supporting a user in a relaxing posture;
   multiple built-in speakers built into the body-supporting structure, arranged to be in physical contact with the user and to transfer vibrational output to multiple respective locations of the user's body, wherein the built-in speakers are isolated from each other to contain vibrational output from each built-in speaker to a respective location;
   one or more input devices comprising at least one input device that is an oscillator driving the headphones and the built-in speakers; and a computing device connected to the at least one biometric measurement device, to the headphones, and to the built-in speakers, and configured to send different outputs by the one or more input devices to the headphones and to the built-in speakers in accordance with the state detected.

2. The system of claim 1, wherein the at least one biometric measurement device is at least one of an EEG system, an ultrasound transducer, a heart rate monitor, and a breathing monitor.

3. The system of claim 1, further comprising a virtual reality display, and wherein the computing device is further configured to synchronize visuals displayed on the virtual reality display with output of the headphones and the built-in speakers.

4. The system of claim 1, wherein the computing device is at least one of a smartphone, tablet, laptop, desktop and built-in computer.

5. The system of claim 1, wherein at least one of the built-in speakers is an ultrasound transducer producing ultrasound frequencies above 20,000 Hz.

6. The system of claim 1, wherein one of the one or more input devices is for selecting from a computer display a specific body area to be treated by the vibrational output.

7. The system of claim 1, wherein the body-supporting structure further comprises a heating blanket.

8. The system of claim 1, wherein the oscillator is configured to produce binaural beats.

9. The system of claim 8, wherein the binaural beats are approximately 0.1 Hz to approximately 30 Hz.

10. A method for providing multisensory stimulation, comprising:
    providing a body-supporting structure;
    placing a user in physical contact with the body-supporting structure;
    measuring a user's state with at least one biometric measurement device;
    transferring an auditory stimulus in accordance with the state detected to headphones on the user;
    providing vibrations to multiple areas of the user's body from multiple respective built-in speakers of the body-supporting structure, in accordance with the state detected, wherein the multiple respective built-in speakers are isolated from each other to isolate vibrational output from each speaker to its respective location;
    configuring an oscillator to produce binaural beats from the headphones; and
    selecting one body area to receive vibrations according to a selection by a user of a body area displayed on a computer display.

11. The method of claim 10, wherein the at least one biometric measurement device is at least one of an EEG system, an ultrasound transducer, a heart rate monitor, and a breathing monitor.

12. The method of claim 10, wherein at least one of the multiple respective speakers is an ultrasound transducer producing ultrasound frequencies above 20,000 Hz.

13. The method of claim 10, wherein the vibrations are provided with frequencies up to approximately 20,000 Hz.

14. The method of claim 10, further comprising a virtual reality display to the user synchronized with the auditory stimulus and with the vibrations output to multiple body areas.

15. The method of claim 10, wherein the binaural beats are provided at approximately 0.1 Hz to approximately 30 Hz.

16. The method of claim 10, wherein transferring the auditory stimulus and providing the vibrations in accordance with the state detected comprises transmitting different auditory and vibrational signals to each of the headphones and speakers in accordance with the state detected.

17. The method of claim 10, wherein transferring the auditory stimulus further comprises creating a surround sound space from the headphones.

* * * * *